(12) United States Patent
Smith et al.

(10) Patent No.: US 6,736,958 B1
(45) Date of Patent: May 18, 2004

(54) ION SENSING METHOD

(75) Inventors: Richard Harding Smith, Dexter, MI (US); Glenn Brian Martin, Farmington Hills, MI (US)

(73) Assignee: IA INC, Ann Arbor, MI (US)

( * ) Notice: Subject to any disclaimer, the term of this patent is extended or adjusted under 35 U.S.C. 154(b) by 0 days.

(21) Appl. No.: 09/836,542

(22) Filed: Apr. 18, 2001

Related U.S. Application Data (60) Provisional application No. 60/198,444, filed on Apr. 19, 2000.

(51) Int. Cl.$^7$ .................. G01N 27/333; G01N 27/447; G01N 30/02
(52) U.S. Cl. ............... 205/789; 210/656; 210/633; 210/634; 210/660; 435/288.6; 422/82.03; 436/161; 423/181; 423/21.5; 423/24; 423/49
(58) Field of Search .................. 205/789, 789.5, 205/793.5; 204/416, 419, 461, 452, 603, 612, 601, 401; 422/70, 82.03; 210/633, 634, 635, 656, 660; 435/288.6; 436/161; 423/181, 8, 21.5, 24, 49

(56) References Cited

U.S. PATENT DOCUMENTS 6,126,801 A 10/2000 Sokalski et al.

FOREIGN PATENT DOCUMENTS

JP 59-163557 * 9/1984

OTHER PUBLICATIONS

Smith et al. ("Monitoring of trace levels of perchlorate by ion chromatography and an ion selective electrode," Abstracts of Papers—American Chemical Society (2000), 220 th, ENVR–252.*

JPO abstract of JP 59–163557 A (Shirai et al.).*

Kappers et al. ("Potentiometric detection of inorganic anions and cations in capillary electrophoresis with coated wire ion–selective electrodes," Analytica Chimica Acta 350 (1997) 141–147).*

Lowering the Detection Limit of Solvent Polymeric Ion–Selective Electrodes. 1. Modeling the Influence of Steady–State Ion Fluxes, Tomasz Sokalski et al, Analytical Chemistry, vol. 71, No. 6, Mar. 15, 1999.

(List continued on next page.)

*Primary Examiner*—Alex Noguerola
(74) *Attorney, Agent, or Firm*—Donald K. Wedding; Jim Zegeer (57) ABSTRACT

The present invention allows the determination of trace levels of ionic substances in a sample solution (ions, metal ions, and other electrically charged molecules) by coupling a separation method, such as liquid chromatography, with ion selective electrodes (ISE) prepared so as to allow detection at activities below $10^{-6}$M. The separation method distributes constituent molecules into fractions due to unique chemical and physical properties, such as charge, hydrophobicity, specific binding interactions, or movement in an electrical field. The separated fractions are detected by means of the ISE(s). These ISEs can be used singly or in an array. Accordingly, modifications in the ISEs are used to permit detection of low activities, specifically, below $10^{-6}$M, by using low activities of the primary analyte (the molecular species which is specifically detected) in the inner filling solution of the ISE. Arrays constructed in various ways allow flow-through sensing for multiple ions.

12 Claims, 8 Drawing Sheets

OTHER PUBLICATIONS

Lowering the Detection Limit of Solvent Polymeric Ion–Selective Membrane Electrodes. 2. Influence of Composition of Sample and Internal Electrolyte Solution, Tomasz Sokalski et al, Analytical Chemistry, vol. 71, No. 6, Mar. 15, 1999.

Lead–Selective Bulk Optodes Based on Neutral Ionophores with Subnanomolar Detection Limits, Markus Lerchi, et al. Analytical Chemistry 1992, 64, Jul. 15, 1992.

Potentiometric pH Detection in Suppressed Ion Chromatography, Marek Trojanowicz, et al, Anal.Chem (1989) 61, 787–789, Apr. 1, 1989.

Replacement Ion Chromatography with Potentiometric Detection Using a Potassium–Selective Membrane Electrode, Marek Trojanowicz et al. Analytical Chimica Acta, 222 (1989) 95–107, month unknown.

Fast Determination of Anions by Computerized Ion Chromatography Coupled with Selective Detectors, J. Slanina, et al, Analytica Chimica Acta, 130 (1981) 1–8, month unknown.

Determination of Monovalent Cations by Ion chromatography with Ion–Selective Electrode Detection, Koji Suzuki, et al, Anal. Chem. 55, (1983) 2011–2013, Oct. 1983.

Direct and Replacement Ion Chromatography With Potentiometric Detection Using a Silver/Silver Bromide Electrode, Marek Trajanowicz, Analytica Chimica Acta, 222 (1989) 109–119, month unknown.

Potentiometric detection in ion chromatography using multi–ionophore membrane electrodes, Sang Hyun Han, et al, Journal of Chromatography 648 (1993) 283–288, month unknown.

Nonlinear Calibration of Ion–Selective Electrode Arrays for Flow Injection Analysis, Robert J. Forster et al., Anal. Chem 1992, 64, 1721–1728, Aug. 01, 1992.

* cited by examiner

ION SENSING METHOD

CROSS-REFERENCES TO RELATED APPLICATIONS

This application clams benefit of provisional patent application No. 60/198,444, Apr. 19, 2000, by Richard H. Smith and Glenn B. Martin

STATEMENT REGARDING FEDERALLY SPONSORED RESEARCH OR DEVELOPMENT

The technology developed under this patent was developed under two Federally sponsored contracts:

Perchlorate Monitoring by Portable Sensing Technology. Air Force Contract #F08637-99-C-6013 (P. I. Richard H. Smith, Ph.D.).

Real-time Array Sensor System for Field Monitoring of Metal Ions. Department of Energy Contract #DE-FG02-00ER83019 (P. I. Richard H. Smith, Ph.D.).

REFERENCE TO A "MICROFICHE APPENDIX"

Not applicable

BACKGROUD OF THE INVENTION

1. Field of the Invention

Many methods of analyzing chemical species are based on means of separation, in which the constituent molecules within a sample are separated into groups, mediated by their particular physical and chemical properties. In certain of these methods, such as chromatography and capillary electrophoresis, the methods used to detect the presence of separated molecules typically ale nonspecific, that is, they do not discriminate a particular target analyte from all other molecules in the sample. Discrimination results only from the separation event. Such methods may yield false results in the event that a different molecular species should become partitioned into the same volume or otherwise come into the same location as the authentic target molecule. Due to the nonspecific detection of such methods, there is no descrimination between the authentic target molecule and other molecular species, and false assignment of analytical results from a sample can cause inappropriate action to ensue. To address the lack of detection specificity in such methods, this invention provides a specific detection means, particularly the use of an ISE (ion selective electrode) as the detection device. In addition, many analytical methods require the detection of molecular species at concentrations in the range $\mu g/L$ ($10^{-6}$ grams/liter) and below (equivalent to parts per billion, or ppb), or $10^{-6}$ M (moles/liter) and below. Certain modifications can be made in the construction of an ISE that will permit detection of molecular species in the range $\mu g/L$ and below. This invention thus addresses the particular need for selective detection following a separation method, by coupling of a modified ISE to a separation method, and allows the specific detection of molecular species in the range below mg/L or micromoles/liter.

2. Description of the Related Art

Separation of molecules of interest within a mixture is a widely explored means of analyzing chemical species. There exist many such methods, including variations of chromatography such as liquid chromatography, gas chromatography and thin-layer chromatography, in which separation occurs due to the physical and chemical nature of the interactions between the constituent molecules and both a solid support and a liquid or gaseous flow stream in which the sample is dissolved. Thus, separation occurs due to differences in the physical and chemical nature of the target molecule compared to other molecules within the sample. A specific example of this method is ion chromatography (IC), wherein charged ionic molecules can be separated from one another on a column of opposite charge, with separation due to differences in the nature of the charge and of other physical features of the molecules. Electrophoresis is a similar method, wherein an electrical field is applied across the solid support and separation occurs due to electrical properties of the constituent molecules within the sample. A specific example of this method is capillary electrophoresis, wherein a sample is injected into a thin capillary tube and an electric field is applied, resulting in differential migration of molecules in the sample.

The above mentioned separation methods, chromatography and electrophoresis, have been used in conjunction with specific detection methods. Liquid chromatography L for ions (IC, or ion chromatography) frequently is followed by detection using suppressed conductivity (Fresenius, 1988; Okamoto. 1999) or devices that measure electromagnetic properties such as absorption Or emission of light at certain wavelengths; detection by man spectrometry is used to further subdivide molecules into charged fragments. Potentiometric detection of LC has been reported using conventional electrodes, which typically have detection limits in the range of $\mu mol/L$ ($10^{-6}$ moles/liter) or ppm (parts per million, or mg/L) (Picioreanu, 2000). Potentiometric detection has been used following capillary electrophoresis, again having detection limits in the range of $\mu mol/L$ or ppm (Schnierle, 1998). A particular challenge heretofore unmet relates to the low concentrations of molecular species that frequently are of interest. Although many analytes of interest are found at concentrations in the range of ppb or nmol/L ($10^{-9}$ M), until recently there have been no reports of methods to reduce the minimum detectable concentration for ISEs below approximately the ppm level. However, a recent report (Sokalski, 1999) described a method for greatly reducing the detection limit for ISEs, based on reduction of the concentration of primary ion in the internal electrolyte solution, and in an equilibrium or steady-state mode. This method has not been used as a specific detector for chromatography, electrophoresis or other separation means. Therefore, one novel claim of the sent invention is the use of ion selective electrodes, modified to allow detection of specific ionic spies in the range of nmol/L and below, with such ISEs used as detectors following a separation method.

A variety of m fabricated array sensors have been developed for detection of multiple ionic species in complex mixtures, such as clinical and environmental samples (Lindner, 2000). In addition, the method has not been used in an array sensor, where a bank of specific ISEs serves to detect ionic specific ionic species after their separation from a complex mixture. The novel claim of the present invention is the use of suitably modified ISEs as detectors following chromatography, electrophoresis or other separation methods.

The following is a list of related prior art, some of which has been discussed above:

Fresenius, W, Quentin, K E, and Schneider, W. Water Analysis (Berlin: Springer-Verlag, 1988)174–181.

Lindner E, Buck R P. Microfabricated potentiometric electrodes and their in vivo applications. Anal Chem 72:336A-45A (2000).

Okamoto, H S, Rishi, D K, Steeber, W R, et al Using ion chromatography to detect perchlorate. J Amer Waterworks Assoc 91(10), 73–84 (1999).

Picioreanu S. Poels I, Frank J, van Dam J C, van Dedem G W K, Nagels, L J. Potentiometric detection of carboxylic acids, phosphate esters, and nucleotides in liquid chromatography using anion-selective coated-wire electrodes. Anal Chem 72:2029–34, (2000).

Schnierle P, Kappes T, Hauser P C. Capillary electrophoretic determination of different classes of organic ions by potentiometric detection with coated-wire-ion-selective electrodes. Anal Chem 70:3585–9 (1998).

Sokalski T, Zwicki T, Baker E, and Pretsch E. Lowering the detection limit of solvent polymeric ion-selective electrodes. 1. Modeling the influence of steady-state ion fluxes. Anal. Chem. 71, 1204–9 (1999).

Sokalski T. Pretsch E. Low Detection Limit Ion Selective Membrane Electrodes. U.S. Pat. No. 6,126,801, Oct. 3, 2000.

BRIEF SUMMARY OF THE INVENTION

The invention utilizes recent advances which greatly improve the detection limits of ion selective electrodes, using such electrodes for the detection of ionic species which have been separated by chromatographic, electrophoretic, or other means. The new method can be used, e.g., in field studies for monitoring of metal ions at below $10^{-6}$ M when there are other contaminating ions present at concentrations which would interfere with direct measurement of the primary ion.

BRIEF DESCRIPTION OF THE SEVERAL VIEWS OF THE DRAWINGS

response (mV)=0.328[perchlorate]+0.081

$R^2$=0.995.

DETAILED DESCRIPTION OF THE INVENTION

According to this invention, additional ISEs can be used which are specific for any ion or other charged molecule, based upon specific complexation chemistry between the primary analyte and a specific complexation agent which resides in a polymeric layer in the electrode. The ion-selective or molecule-selective polymeric layer thus extracts the primary ion from the flow stream. Measurement of the concentration results from determining the difference in electrical potential between the ISE and a reference electrode which is bathed in the same sample solution. The sample solution acts as a liquid junction, and can be comprised of any available reference electrode.

Specifications

Figure 1:
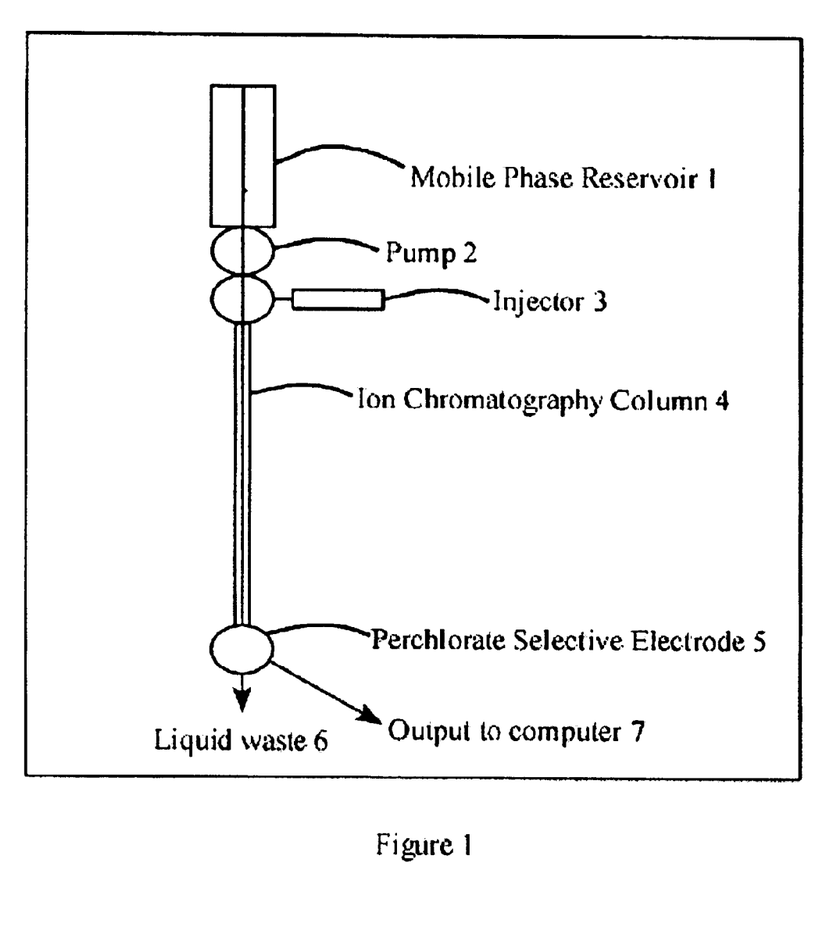
FIG. 1 shows the modified ISE used as a detector following separation methods such as chromatography or electrophoresis, This shows a perchlorate sensor using a perchlorate ISE with separation performed by IC, which comprises a mobile phase reservoir 1, pump 2, injector 3, ion chromatography column 4, and perchlorate selective electrode 5.
Figure 2:
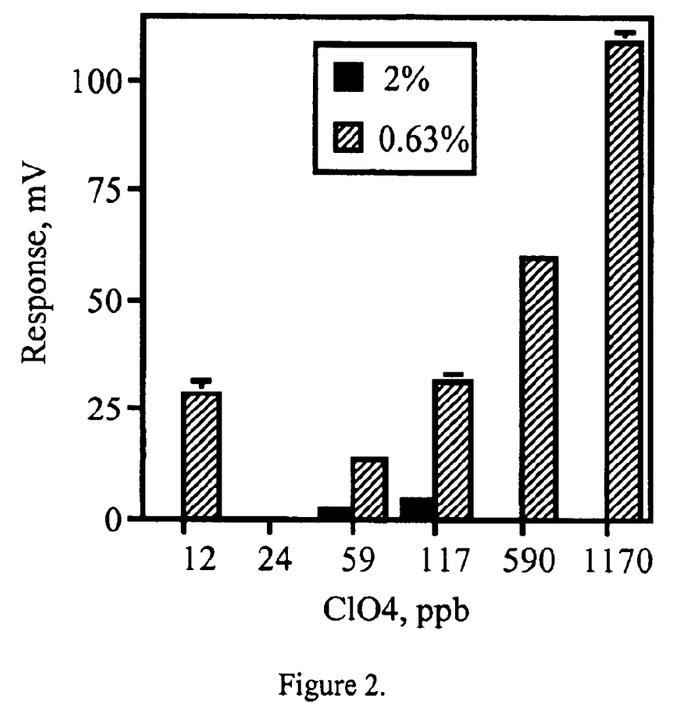
FIG. 2 shows electrode response as a function of the concentration of the specific ionophore in the ISE. In this example, electrode composition is: 2% TOPB, 30% PVC and 68% nPOE (black bars); 0.63% TOPB, 30% PVC and 69.4% nPOE (light gray bars). Internal electrode solution: 20 mM $Na_2SO_4$, 0.1 µM $NH_4ClO_4$. Measurements were made under flow conditions at 0.5 ml/min at room temperature. Here, TOPB is tetraoctyl phosphonium bromide, PVC is poly(vinyl) chloride, and nPOE is nitrophenyl octyl ether.
Figure 3:
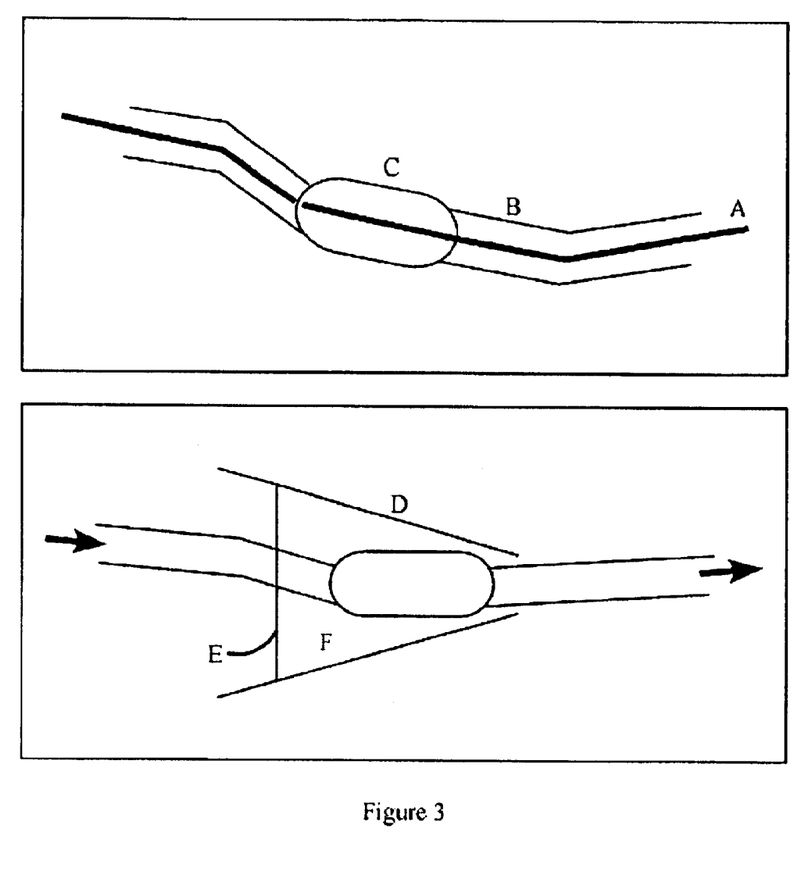
FIG. 3 shows laboratory construction of tubular ISEs as an example of construction of the ISES. Above, monofilament line (A) is passed through sections of tubing (B), and the membrane cocktail, containing the specific ion exchanger, is applied to the gap between tubing sections (C). Below, the monofilament line is removed and the ISE placed in a pipet tip (D) along with the internal electrolyte (F), which is kept from evaporating by a plug of epoxy potting compound (E). Multiple sensing regions can be constructed using sensing regions arranged serially or in parallel.

ISE composition. The modified ISE is composed of the following materials: a polymer matrix such as poly(vinyl) chloride (PVC), polyolefins or other hydrophobic polymers; a plasticizer, such as nitrophenyl octyl ether (nPOE), DOS (dioctyl sebacate), other ether plasticizers or other plasticizers; and a specific complexing and chelating agent, such as for anions: tetraoctyl phosphonium bromide (TOPB), nitrophenyloctyl ether, nitron, or tetraalkylammonium salts and for cations: crown ethers, cryptands and other cage compounds, lipophilic nitrogenous ethers of oxygen and sulfur, or other metal ion-selective ionophores. The ISE can further be composed of various copolymers of acrylic acid, carboxy elastomers, or substituted polyvinyls. The perchlorate ISE described herein may be made from 10–80% by weight PVC, typically 30% PVC; 20–90% by weight nPOE, typically 70% nPOE; and 0.1 to 5% by weight TOPB, typically 0.63% TOPB. Experimental data illustrating the determination of perchlorate with an ISE using two different concentrations of TOPB is shown in FIG. 2. The cesium ISE described herein may be made from 10–80% by weight PVC, typically 30% PVC; 20–90% by weight DOS, typically 70% DOS; and 0.1 to 5% by weight cesium-specific ionophore (calix[6]arene-hexaacetic hexaethyl ester), typically 1.0% cesium ionophore. These components are dissolved in an appropriate solvent, such as THF (tetrahydrofuran) or cyclohexane.

Construction of tubular-flow-through electrodes. Narrow-bore tubing, such as PVC tubing (ID=0.014 inches) is used for the flow-cell ISEs. In one favored construction, two small pieces of PVC tubing are threaded onto a nylon monofilament line, leaving a gap of ~5 mm. The membrane cocktail is applied between proximal ends of tubing and is allowed to dry. The nylon monofilament line is removed and, to protect the sensing surface, electrodes are placed within a 1000 $\mu$L pipet tip, a length of stranded 24 ga. aluminum wire or other conductive wire is inserted, the internal electrolyte solution is added and the pipet tip is sealed with epoxy potting compound. As an example of a tubular flow-through electrode for perchlorate, in the preferred configuration, the internal electrolyte solution consists of 0.2 to 200 mM $Na_2SO_4$, but preferably 20 mM $Na_2SO_4$, and 0.01 to 100 $\mu$M $NH_4ClO_4$, typically 0.1 $\mu$M $NH_4ClO_4$.

Modification of detection limit by varying internal electrode solution. The internal electrode solution for an ISE is the liquid solution that bathes the side of the selective membrane opposite the sample side, and which forms a liquid junction with a wire used to measure the electrical potential of the ISE in comparison to the reference electrode. By routine practice, internal electrolyte solutions for ISEs contain some level of the primary analyze whose concentration in standard configurations is quite high. Recent studies have demonstrated that varying the concentration of the analyte can alter detection limits for ISE in equilibrium solution by several orders of magnitude. These computational modeling studies indicate that varying the concentration of the primary ion in the meal electrolyte solution can vary the response to the primary ion in the sample. Thus, trace levels of ions (low $\mu$g/L) may be measured only when a suitable match has been made with the concentration of the primary ion in the inner electrode solution. The current invention expands on the principle and adds novelty in the use of ISEs having low $\mu$g/L detection limits, particularly using the ISE as a flow-cell detector for chromatography and other separation methods.

Figure 4:
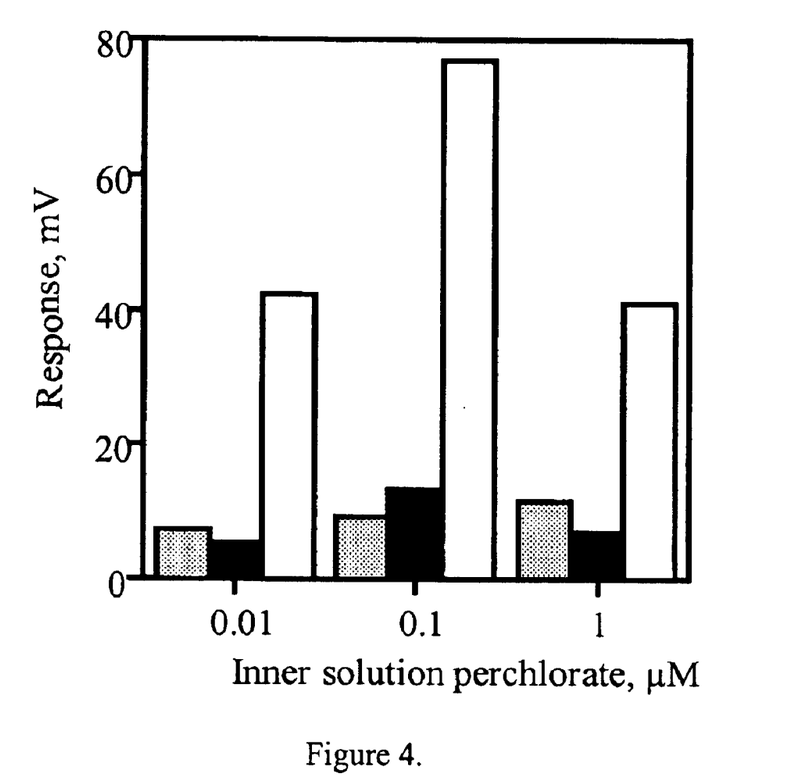
FIG. 4 shows that electrode response vanes with inner solution perchlorate concentration. Electrodes responded to varying levels of perchlorate in the sample: 10 (shaded), 100 (black) and 1000 (white) µg/L. Average of three injections, with coefficients of variation (CV) less than 10%.

Based on the above considerations, the concentration of perchlorate in the inner filing solution was studied using a perchlorate ISE. Electrodes were filled with solutions containing 0.2 mM $Na_2SO_4$ and 0.01, 0.1 or 1.0 $\mu$M $NH_4ClO_4$ (1, 10 or 100 ppb, respectively). As shown in FIG. 4, when the electrode inner solution had a perchlorate concentration of 0.1 $\mu$M (10 ppb), response to perchlorate in the sample gave logarithmic dose dependence at a low concentration range. This demonstration shows that the equilibrium ISE principle can equally be applied to a flow-cell configuration.

Description of the separation method. A wide variety of separation methods are available which will separate complex mixture into discrete fractions, including chromatography, electrophoresis, selective complexation, selective extraction, liquid-liquid extraction. The example used in the current invention is separation by ion chromatography (IC), with specific examples given for the measurement of perchlorate and of cesium using IC methods which were optimized for anions and for cations, respectively. Thus, to perform IC with detection by the ISE (IC-ISE), separation of perchlorate is performed on an anion exchange column, while separation of cesium is performed on a cation exchange column.

Demonstration of the Use of the Perchlorate IC-ISE in the Presence of Other Anions.

Figure 5:
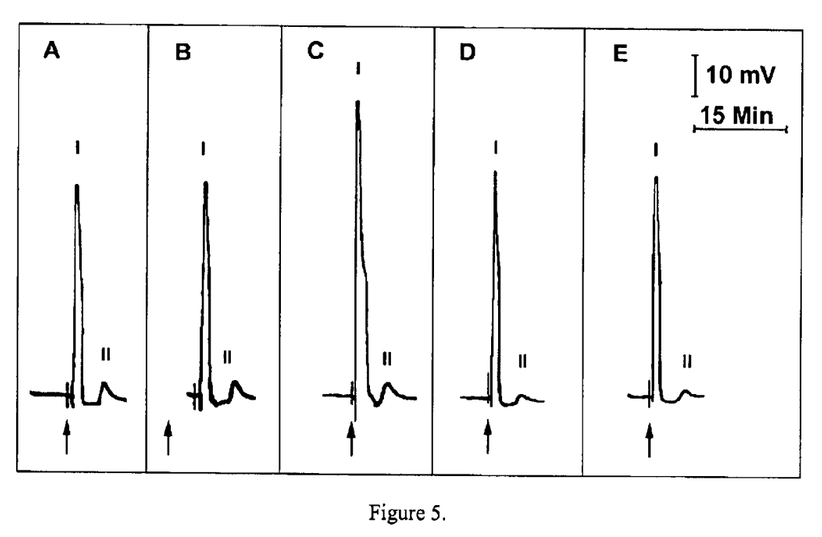
FIG. 5 shows the measurement of low ppb perchlorate in buffered solutions. Interferents are in peak I ad perchlorate in peak II in each chromatogram; arrows indicate injection. A: 18 ppb perchlorate, 192 ppm sulfate; B: 18 ppb perchlorate, 355 ppm chloride, 192 ppm sulfate; C: 18 ppb perchlorate, 1000 ppm chloride, 192 ppm sulfate; D and E: 10 ppb perchlorate, 355 ppm chloride, 192 ppm sulfate.

The principal utility of the current invention is for the determination of low concentrations ($\mu$g/L or ppb) or ionic species in complex mixtures. In one specific example, measurement of perchlorate in groundwater using the perchlorate IC-ISE is illustrated in water samples having very high concentrations of other anions along with perchlorate, including chloride and sulfate. FIG. 5 illustrates the detection of perchlorate in water samples of known composition containing perchlorate at 10 and 18 $\mu$g/L. Perchlorate is the second peak in each chromatogram, eluting in about 8 minutes under these conditions. The presence of sulfate or chloride up to 1000 ppm (mg/L) had no measurable impact on the ability to detect perchlorate.

Figure 6:
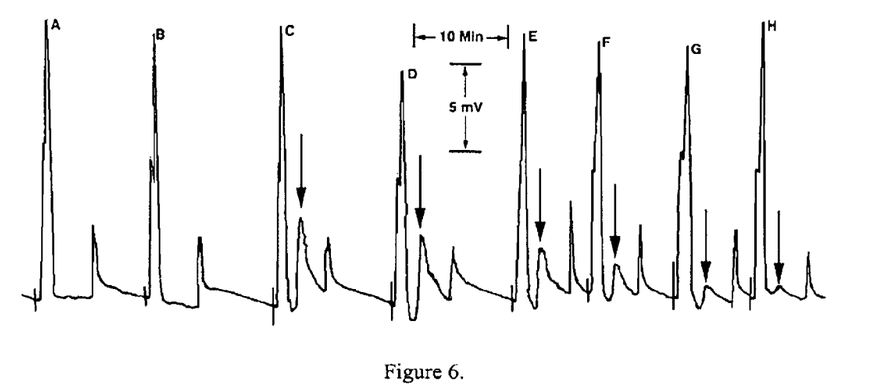
FIG. 6 shows the measurement of perchlorate in groundwater. The IC-ISE responds to perchlorate levels as low as 2.5 ppb in groundwater samples. Perchlorate was spiked into the samples at 0 (A and B), 20 (C and D), 15 (E), 10 (F), 5 (G) and 2.5 (H) ppb.
Figure 7:
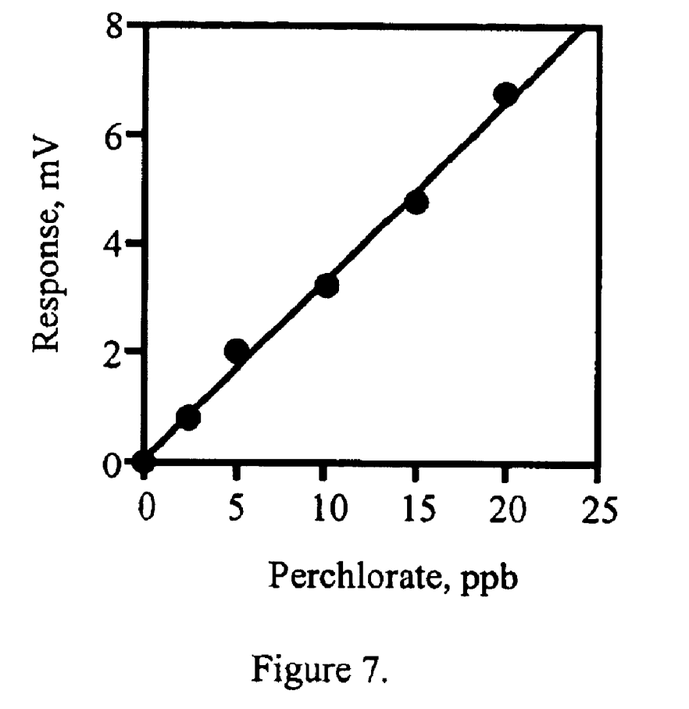
FIG. 7 shows a calibration curve for perchlorate response. Data in this graph were taken from the peak responses for each chromatogram in FIG. 6. Equation of the linear regression line.

Another example of the use of the invention is in the determination of a specific ion in a very complex mixture. In this example, the perchlorate IC-ISE is used to determine perchlorate spiked into groundwater samples whose composition is largely unknown. Well water was spiked it to 0, 2.5, 5, 10, 15 or 20 $\mu$g perchlorate. FIG. 6 illustrates the detection of perchlorate within this complex mixture. The IC-ISE gave a linear response to perchlorate with an excellent correlation coefficient (FIG. 7), indicating that interpolation of experimental results with the IC-ISE will be straightforward.

Demonstration of the Measurement of Cesium in Groundwater.

Figure 8:
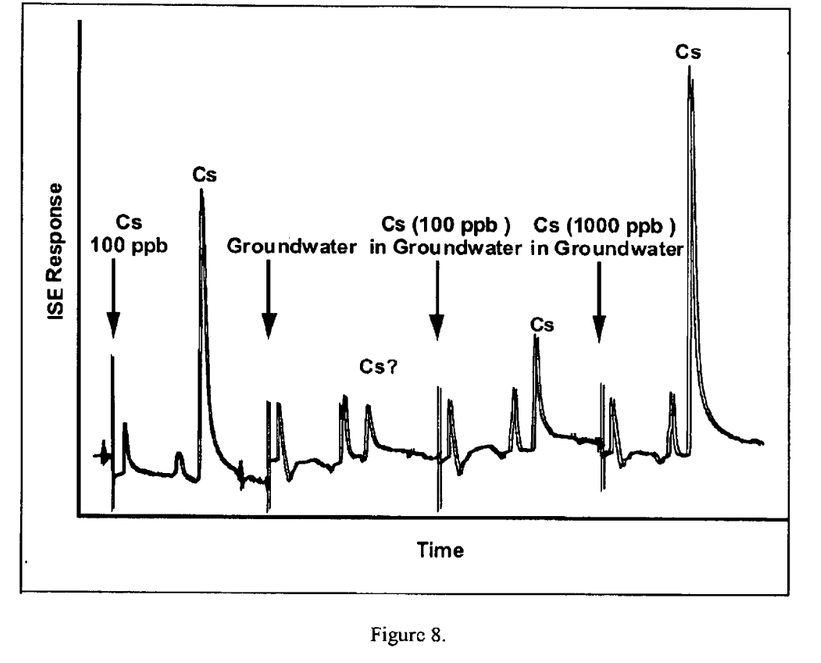
FIG. 8 shows IC-ISE determination of cesium spiked into groundwater. From the left: injection of 100 ppb cesium; injection of fly drawn groundwater, injection of 100 ppb cesium spiked into groundwater; injection of 1000 ppb cesium injected into groundwater

Another example of the utility of this invention is the determination of metal ions in groundwater. In this example, well water was spiked with known quantities of cesium. A sample of 100 ppb cesium was first injected to check system response and retention time (FIG. 8). Groundwater was then injected to obtain a background chromatogram. From the peak at the retention time of cesium, it appears that the groundwater contains an appreciable concentration of cesium. The groundwater was then spiked with 100 and 1000 ppb cesium and ran on the column. Compared to the 100 ppb cesium standard, the groundwater spiked with 100 ppb cesium did not produce nearly as large a response, indicating that the added cesium does not remain in the free form and is completed or otherwise sequestered. The groundwater sample spiked with 1000 ppb cesium showed a very large response at the appropriate retention time. The results from the cesium spiking experiments are consistent with the presence of an anionic inorganic species which precipitated the added cesium up to approximately 100 ppb, but was overcome when the sample was spiked with 1000 ppb cesium. Based upon this method of internal standardization, the cesium concentration in the well water was estimated to be on the order of 10 ppb.

Ions of Environmental Concern.

This invention can be used to determine the activity of ionic substances of environmental concern, selected from the group $Cs^+$, $UO_2^{2+}$, $Sr^{2+}$, $PuO_2^+$, $Pb^{2+}$, $Hg^{2+}$, $Hg_2^{2+}$, $Cu^{2+}$, $Cu^+$, $Ag^+$, $ClO_4^-$, $NO_3^-$, $NO_2^-$, $AsO_4^-$, $AsO_3^-$, and $TcO_4^-$.

This invention allows analysis of a complex aqueous sample consisting of interfering ionic species present in activities sufficient to cause a greater than 1% error in the determination of activity of the ionic substance of interest.

What is claimed is:

1. In a method for determination of an ionic substance in a complex aqueous matrix, the improvement which comprises separating at least one ionic substance having an activity below $10^{-6}$M with a separation method and detecting said at least one ionic substance with a low detection limit ion selective electrode having an internal electrolyte solution.

2. The invention of claim 1 wherein the separating method is selected from the group consisting of chromatography, electrophoresis, selective complexation, selective extraction and liquid-liquid extraction.

3. The invention of claim 2 wherein the ionic substance to be determined is one or more ions of environmental concern selected from the group consisting of $Cs^+$, $UO_2^{2+}$, $Sr^{2+}$, $Pb^{2+}$, $Hg^{2+}$, $Hg_2^{2+}$, $Cu^{2+}$, $Cu^+$, $Ag^+$, $ClO_4^-$, $NO_2^-$, $NO_3^-$, $AsO_4^-$, $AsO_3^-$, and $TcO_4^-$.

4. In a method for monitoring the activity of the ionic substance in an eluent, the improvement which comprises measuring the activity below $10^{-6}M$ for an ionic substance of interest by:
   a. separating into fractions a standard solution of known concentration of the ionic substance of interest;
   b. selectively measuring the electrical potential of the different fractions of the standard solution with an ion selective electrode so as to determine the eluent volume of the ionic substance of interest;
   c. separating a complex sample into eluent fractions, at least one of which contains an unknown concentration of the ionic substance of interest present with an activity below $10^{-6}M$ and
   d. selectively measuring the electrical potential of the eluent fractions with an ion selective electrode having an internal electrolyte solution so as to determine the activity of the ionic substance of interest.

5. The invention of claim 4 wherein each separating step a and c is selected from the group consisting of chromatography, electrophoresis, selective complexation, selective extraction, and liquid-liquid extraction.

6. The invention of claim 4 wherein the ionic substance to be determined is one or more ions of environmental concern selected from the group consisting of $Cs^+$, $UO_2^{2+}$, $Sr^{2+}$, $Pb^{2+}$, $Hg^{2+}$, $Hg_2^{2+}$, $Cu^{2+}$, $Cu^+$, $Ag^+$, $ClO_4^-$, $NO_2^-$, $NO_3^-$, $AsO_4^-$, $AsO_3^-$, and $TcO_4^-$.

7. In a method for monitoring the activity of an ionic substance of interest in an eluent, the improvement for measuring the activity of the ionic substance below $10^{-6}M$ by means of internal standardization which comprises;
   a. separating a first portion of a complex sample into eluent fractions, at least one of which contains an unknown concentration of the ionic substance of interest below $10^{-6}M$;
   b. selectively measuring the electrical potential of the eluent fractions with an ion selective electrode;
   c. spiking a second portion of the complex sample with a known concentration of the ionic substance of interest;
   d. separating the spiked complex sample into eluent fractions;
   e. selectively measuring the electrical potential of the eluent fractions of the spiked sample with an ion selective electrode having an internal electrolyte solution; and
   f. comparing the measurements of (b) and (e) so as to determine the activity of the ionic substance of interest.

8. The invention of claim 7 wherein each separating step a and d is selected from the group consisting of chromatography, electrophoresis, selective complexation, selective extraction, and liquid-liquid extraction.

9. The invention of claim 7 wherein the ionic substance to be determined is one or more ions of environmental concern selected from the group consisting of $Cs^+$, $UO_2^{2+}$, $Sr^{2+}$, $Pb^{2+}$, $Hg^{2+}$, $Hg_2^{2+}$, $Cu^{2+}$, $Cu^+$, $Ag^+$, $ClO_4^-$, $NO_2^-$, $NO_3^-$, $AsO_4^-$, $AsO_3^-$, and $TcO_4^-$.

10. In a method for monitoring the activity of an ionic substance of interest in an eluent, the improvement for measuring the activity of the ionic substance below $10^{-6}M$ by means of internal standardization which comprises;
    a. separating a first portion of a complex sample into eluent fractions, at least one of which contains an unknown concentration of the ionic substance of interest below $10^{-6}M$;
    b. selectively measuring the electrical potential of the eluent fractions with an ion selective electrode having an internal electrolyte solution;

spiking a second portion of the complex sample with a known concentration of an ionic substance which is dissimilar to the ionic substance of interest;
    d. separating the spiked complex sample into eluent fractions;
    e. selectively measuring the electrical potential of the eluent fractions of the spiked sample with said ion selective electrode; and
    f. comparing the measurements of (b) and (e) so as to determine the activity of the ionic substance of interest.

11. The invention of claim 10 wherein each separating step a and d is selected from the group consisting of chromatography, electrophoresis, selective complexation, selective extraction, and liquid-liquid extraction.

12. The invention of claim 10 wherein the ionic substance to be determined is one or more ions of environmental concern selected from the group consisting of $Cs^+$, $UO_2^{2+}$, $Sr^{2+}$, $Pb^{2+}$, $Hg^{2+}$, $Hg_2^{2+}$, $Cu^{2+}$, $Cu^+$, $Ag^+$, $ClO_4^-$, $NO_2^-$, $NO_3^-$, $AsO_4^-$, $AsO_3^-$, and $TcO_4^-$.

* * * * *